(12) United States Patent
Caldarone

(10) Patent No.: US 10,098,779 B2
(45) Date of Patent: Oct. 16, 2018

(54) TREATMENT OF ERECTILE DYSFUNCTION USING REMOTE ISCHEMIC CONDITIONING

(71) Applicant: The Hospital for Sick Children, Toronto (CA)

(72) Inventor: Christopher Caldarone, Toronto (CA)

(73) Assignee: The Hospital for Sick Children, Toronto (CA)

( * ) Notice: Subject to any disclaimer, the term of this patent is extended or adjusted under 35 U.S.C. 154(b) by 182 days.

(21) Appl. No.: 14/773,919

(22) PCT Filed: Mar. 12, 2014

(86) PCT No.: PCT/IB2014/000922
§ 371 (c)(1),
(2) Date: Sep. 9, 2015

(87) PCT Pub. No.: WO2014/140832
PCT Pub. Date: Sep. 18, 2014

(65) Prior Publication Data
US 2016/0015553 A1     Jan. 21, 2016

Related U.S. Application Data

(60) Provisional application No. 61/801,006, filed on Mar. 15, 2013.

(51) Int. Cl.
| A61F 5/00 | (2006.01) |
| A61F 5/41 | (2006.01) |
| A61H 1/00 | (2006.01) |
| A61H 9/00 | (2006.01) |

(52) U.S. Cl.
CPC .............. *A61F 5/41* (2013.01); *A61H 1/008* (2013.01); *A61H 9/0078* (2013.01); *A61F 2005/414* (2013.01); *A61F 2005/415* (2013.01)

(58) Field of Classification Search
CPC . A61F 5/41; A61F 2005/414; A61F 2005/418
USPC .................................................... 600/38–41
See application file for complete search history.

(56) References Cited

U.S. PATENT DOCUMENTS

| 3,552,383 A | 1/1971 | Krueger et al. |
| 4,106,002 A | 8/1978 | Hogue, Jr. |
| 4,206,764 A | 6/1980 | Williams |
| 4,294,261 A | 10/1981 | Baker et al. |
| 4,321,929 A | 3/1982 | Lemelson et al. |
| 4,664,651 A | 5/1987 | Weinshenker et al. |
| 4,690,151 A | 9/1987 | Utsunomiya et al. |
| 5,072,736 A | 12/1991 | Ogawa et al. |
| 5,152,770 A | 6/1992 | Bengmark et al. |
| 5,135,003 A | 8/1992 | Souma |
| 5,267,565 A | 12/1993 | Beard |
| 5,569,304 A | 10/1996 | Ulrich |
| 5,571,075 A | 11/1996 | Bullard |
| 5,634,467 A | 6/1997 | Nevo |
| 5,651,369 A | 7/1997 | Tomita |
| 5,687,732 A | 11/1997 | Inagaki et al. |
| 6,020,334 A | 2/2000 | Fukushi et al. |
| 6,152,881 A | 11/2000 | Raines et al. |
| 6,210,423 B1 | 4/2001 | Kim |
| 6,251,080 B1 | 6/2001 | Henkin et al. |
| 6,303,649 B1 | 10/2001 | Hattori et al. |
| 6,344,025 B1 | 2/2002 | Inagaki et al. |
| 6,485,429 B2 | 11/2002 | Forstner |
| 6,550,482 B1 | 4/2003 | Burbank et al. |
| 6,626,840 B2 | 9/2003 | Drzewiecki et al. |
| 6,650,943 B1 * | 11/2003 | Whitehurst ........ A61N 1/36007 607/39 |
| 6,660,759 B1 | 12/2003 | Hattori et al. |
| 6,670,362 B2 | 12/2003 | Banks et al. |
| 6,702,720 B2 | 3/2004 | Dardik |
| 6,719,704 B2 | 4/2004 | Narimatsu et al. |
| 6,858,012 B2 | 2/2005 | Burns et al. |
| 6,962,599 B2 | 11/2005 | Hui |
| 7,004,907 B2 | 2/2006 | Banet et al. |
| 7,018,335 B2 | 3/2006 | Kario et al. |
| 7,048,702 B2 | 5/2006 | Hui |
| 7,314,478 B2 | 1/2008 | Hui |
| 7,338,410 B2 | 3/2008 | Dardik |
| 7,374,540 B2 | 5/2008 | Schnall |
| 7,390,303 B2 | 6/2008 | Dafni |
| 7,517,312 B2 | 4/2009 | Loeb et al. |
| 7,615,548 B2 | 11/2009 | Gottlieb et al. |
| 7,635,722 B1 | 12/2009 | Bachynsky et al. |
| 7,689,286 B2 | 3/2010 | Pastore et al. |

(Continued)

FOREIGN PATENT DOCUMENTS

| AU | 2011237461 A1 | 11/2012 |
| CA | 2692463 A1 | 1/2009 |

(Continued)

OTHER PUBLICATIONS

Addison et al., Noninvasive remote ischemic preconditioning for global protection of skeletal muscle against infarction. Am J Physiol Heart Circ Physiol. 2003;285:H1435-1443.

Ali et al., Induced remote ischemic pre-conditioning on ischemia-reperfusion injury in patients undergoing coronary artery bypass. J Coll Physicians Surg Pak. Jul. 2010;20(7):427-431.

Ali et al., Remote ischemic preconditioning reduces myocardial and renal injury after elective abdominal aortic aneurysm repair: a randomized controlled trial. Circulation. Sep. 11, 2007;116(11 Suppl):I98-105.

Andreka et al., Remote ischaemic postconditioning protects the heart during acute myocardial infarction in pigs. Heart. Jun. 2007;93(6):749-52. Epub Apr. 20, 2007.

Babak et al., Ischemic Preconditioning as a Possible Factor for Prevention of Restenosis After Coronary Intervention. Sverdlovsk Regional Center of M.V. Savichevsky. Ekaterinburg, Russian Federation. Cardiovascular diseases: scientific conferenceabstracts of the IXth Russian national congress of cardiovascular surgeons. Moscow. Nov. 2003: Bulletin of the Bakoulev Center for Cardiovascular Surgery of the RAMS—2003.—vol. 4, No. 11: 18-21. Russian.

(Continued)

*Primary Examiner* — John Lacyk

(74) *Attorney, Agent, or Firm* — Wolf, Greenfield & Sacks, P.C.

(57) ABSTRACT

The invention contemplates use of remote ischemic conditioning in the treatment of erectile dysfunction.

14 Claims, No Drawings

(56) References Cited

U.S. PATENT DOCUMENTS

| | | | |
|---|---|---|---|
| 7,717,855 B2 * | 5/2010 | Caldarone | A61H 9/0078 600/490 |
| 8,114,026 B2 | 2/2012 | Leschinsky | |
| 8,246,548 B2 | 8/2012 | Naghavi et al. | |
| 8,753,283 B2 | 6/2014 | Leschinsky | |
| D708,338 S | 7/2014 | Ganske et al. | |
| D709,048 S | 7/2014 | Ganske et al. | |
| D709,197 S | 7/2014 | Ganske et al. | |
| 8,764,789 B2 | 7/2014 | Ganske et al. | |
| 8,790,266 B2 | 7/2014 | Caldarone et al. | |
| 8,911,469 B2 | 12/2014 | Raheman | |
| 9,119,759 B2 | 9/2015 | Caldarone et al. | |
| 9,119,761 B2 | 9/2015 | Caldarone et al. | |
| 9,205,019 B2 | 12/2015 | Ganske et al. | |
| 9,393,025 B2 | 7/2016 | Caldarone | |
| 2001/0029389 A1 | 10/2001 | Kim | |
| 2002/0155924 A1 | 10/2002 | Dardik | |
| 2003/0013974 A1 | 1/2003 | Natarajan et al. | |
| 2003/0065270 A1 | 4/2003 | Raines et al. | |
| 2003/0143662 A1 | 7/2003 | Cummings et al. | |
| 2003/0176795 A1 | 9/2003 | Harris et al. | |
| 2003/0216651 A1 | 11/2003 | Burns et al. | |
| 2003/0233118 A1 | 12/2003 | Hui | |
| 2004/0044290 A1 | 3/2004 | Ward et al. | |
| 2004/0064076 A1 | 4/2004 | Bilgi | |
| 2004/0102818 A1 | 5/2004 | Hakky et al. | |
| 2004/0134492 A1 | 7/2004 | Dardik | |
| 2004/0241634 A1 | 12/2004 | Millis et al. | |
| 2004/0255956 A1 | 12/2004 | Vinten-Johansen et al. | |
| 2005/0004476 A1 | 1/2005 | Payvar et al. | |
| 2005/0027218 A1 | 2/2005 | Filtvedt et al. | |
| 2005/0070405 A1 | 3/2005 | Egger | |
| 2005/0159640 A1 | 7/2005 | Barbut et al. | |
| 2005/0177078 A1 | 8/2005 | Loeb et al. | |
| 2006/0024779 A1 | 2/2006 | Cummings et al. | |
| 2006/0052712 A1 | 3/2006 | Poliac et al. | |
| 2006/0052713 A1 | 3/2006 | Poliac et al. | |
| 2006/0052714 A1 | 3/2006 | Poliac et al. | |
| 2006/0058717 A1 | 3/2006 | Hui et al. | |
| 2006/0100639 A1 | 5/2006 | Levin et al. | |
| 2006/0142663 A1 | 6/2006 | Sawanoi et al. | |
| 2006/0167390 A1 | 7/2006 | Hui | |
| 2007/0005106 A1 | 1/2007 | Adducci | |
| 2007/0150005 A1 | 6/2007 | Sih et al. | |
| 2008/0081963 A1 | 4/2008 | Naghavi et al. | |
| 2008/0097385 A1 | 4/2008 | Vinten-Johansen et al. | |
| 2008/0139949 A1 | 6/2008 | Caldarone et al. | |
| 2008/0222769 A1 | 9/2008 | Natonson et al. | |
| 2009/0137884 A1 | 5/2009 | Naghavi et al. | |
| 2009/0192128 A1 | 7/2009 | Worcel et al. | |
| 2009/0221649 A1 | 9/2009 | Krahn et al. | |
| 2009/0238852 A1 | 9/2009 | Kennedy et al. | |
| 2009/0287069 A1 | 11/2009 | Naghavi et al. | |
| 2009/0324748 A1 | 12/2009 | Dobson | |
| 2010/0081941 A1 | 4/2010 | Naghavi et al. | |
| 2010/0105993 A1 | 4/2010 | Naghavi et al. | |
| 2010/0160444 A1 | 6/2010 | Gottlieb et al. | |
| 2010/0160799 A1 | 6/2010 | Caldarone et al. | |
| 2010/0185220 A1 | 7/2010 | Naghavi et al. | |
| 2010/0292619 A1 | 11/2010 | Redington et al. | |
| 2010/0305607 A1 | 12/2010 | Caldarone et al. | |
| 2010/0322467 A1 | 12/2010 | Reed et al. | |
| 2010/0324429 A1 | 12/2010 | Leschinsky | |
| 2010/0328142 A1 | 12/2010 | Zoughi et al. | |
| 2011/0152650 A1 | 6/2011 | Donehoo et al. | |
| 2011/0190807 A1 | 8/2011 | Redington et al. | |
| 2011/0238107 A1 | 9/2011 | Raheman | |
| 2011/0240043 A1 | 10/2011 | Redington | |
| 2011/0251635 A1 | 10/2011 | Caldarone | |
| 2012/0130419 A1 | 5/2012 | Leschinsky | |
| 2012/0265240 A1 | 10/2012 | Ganske et al. | |
| 2012/0277789 A1 | 11/2012 | Caldarone et al. | |
| 2013/0211269 A1 | 8/2013 | Leschinsky | |
| 2013/0317581 A1 | 11/2013 | Redington | |
| 2014/0024986 A1 | 1/2014 | Souma | |
| 2014/0296756 A1 | 10/2014 | Ganske et al. | |
| 2016/0022269 A1 | 1/2016 | Ganske et al. | |
| 2016/0038147 A1 | 2/2016 | Redington | |
| 2016/0038737 A1 | 2/2016 | Redington | |
| 2016/0045726 A1 | 2/2016 | Redington | |
| 2017/0042553 A1 | 2/2017 | Caldarone et al. | |
| 2017/0273695 A1 | 9/2017 | Ganske et al. | |

FOREIGN PATENT DOCUMENTS

| | | |
|---|---|---|
| CN | 2395559 Y | 9/2000 |
| CN | 201098315 Y | 8/2008 |
| CN | 200820123637 | 11/2008 |
| CN | 101317805 A | 12/2008 |
| CN | 201316381 Y | 9/2009 |
| EP | 0 960 598 A1 | 12/1999 |
| EP | 1 016 379 A1 | 7/2000 |
| EP | 1 249 218 A2 | 10/2002 |
| GB | 1323365 A | 7/1973 |
| GB | 2434536 A | 8/2007 |
| JP | 07051276 A | 2/1995 |
| JP | 2001221 A | 1/2001 |
| JP | 2001505472 A | 4/2001 |
| JP | 2002539879 A | 11/2002 |
| RU | 2 253 429 C1 | 6/2005 |
| WO | WO 83/00995 A1 | 3/1983 |
| WO | WO 91/18571 A1 | 12/1991 |
| WO | WO 98/30144 A1 | 7/1998 |
| WO | WO 00/56261 A1 | 9/2000 |
| WO | WO 00/57776 A1 | 10/2000 |
| WO | WO 2004/004702 A2 | 1/2004 |
| WO | WO 2005/011503 A1 | 2/2005 |
| WO | WO 2005/077265 A1 | 8/2005 |
| WO | WO 2006/007851 A2 | 1/2006 |
| WO | WO 2006/024871 A1 | 3/2006 |
| WO | WO 2006/030441 A2 | 3/2006 |
| WO | WO 2006/061825 A2 | 6/2006 |
| WO | WO 2006/069170 A2 | 6/2006 |
| WO | WO 2006/099958 A1 | 9/2006 |
| WO | WO 2007/085828 A1 | 8/2007 |
| WO | WO 2008/070164 A2 | 6/2008 |
| WO | WO 2008/148045 A1 | 12/2008 |
| WO | WO 2008/148062 A1 | 12/2008 |
| WO | WO 2009/010810 A2 | 1/2009 |
| WO | WO 2010/132115 A1 | 11/2010 |
| WO | WO 2011/005538 A2 | 1/2011 |
| WO | WO 2011/121402 A2 | 10/2011 |
| WO | WO 2011/127341 A2 | 10/2011 |
| WO | WO 2012/016280 A1 | 2/2012 |
| WO | WO 2012/090068 A2 | 7/2012 |
| WO | WO 2012/142360 A2 | 10/2012 |

OTHER PUBLICATIONS

Bartekova et al., Liver ischemia induced remote preconditioning: role of cardioprotective proteins. 25. ISHR-ES meeting. Jun. 21-25, 2005. Tromsoe, Norway.J Mol Cell Cardiol. 2005;38(6):1004.

Bauer et al., Does preconditioning protect the coronary vasculature from subsequent ischemia/reperfusion injury? Circulation. Aug. 1993;88(2):659-72.

Bell, Remote ischaemic conditioning and ischaemic heart disease. Br J Hosp Med (Lond). Jan. 2014;75(1):C13-6.

Birnbaum et al., Ischemic preconditioning at a distance:reduction of myocardial infarct size by partial reduction of blood supply combined with rapid stimulation of the gastrocnemius muscle in the rabbit. Circulation. Sep. 2, 1997;96(5):1641-6.

Bøtker et al., Prehospital remote ischemic preconditioning reduces infarct size in patients with evolving myocardial infarction undergoing primary percutaneous intervention. Fondation Leducq Transatlantic Network Presentation. Mar. 2009. 23 pgs.

Botker et al., Remote ischaemic conditioning before hospital admission, as a complement to angioplasty, and effect on myocardial salvage in patients with acute myocardial infarction: a randomised trial. Lancet. Feb. 27, 2010;375(9716):727-34.

Botker et al., Upper-limb ischemia during ambulance transfer reduces myocardial perfusion injury in STEMI. Heartwire. Mar. 28, 2009. Featured at i2 Session of AAC. Mar. 28-31, 2009. Last

(56) References Cited

OTHER PUBLICATIONS

Accessed on Mar. 5, 2012 fromhttp://www.theheart.org/article/951627.do.
Brzozowski et al., Ischemic preconditioning of remote organs attenuates gastric ischemia-reperfusion injury through involvement of prostaglandins and sensory nerves. Eur J Pharmacol. Sep. 19, 2004;499(1-2):201-13.
Calbet et al., Effects of ATP-induced leg vasodilation on VO2 peak and leg O2 extraction during maximal exercise in humans. Am J Physiol Regul Integr Comp Physiol. Aug. 2006;291(2):R447-53. Epub Feb. 16, 2006.
Champion et al., A profile of combat injury. J Trauma. May 2003;54(5 Suppl):S13-9.
Cheung et al., Randomized controlled trial of the effects of remote ischemic preconditioning on children undergoing cardiac surgery: first clinical application in humans. J Am Coll Cardiol. Jun 6, 2006;47(11):2277-82.
Choi et al., Effect of remote ischemic preconditioning on renal dysfunction after complex valvular heart surgery: A randomized controlled trial. J Thorac Cardiovasc Surg. 2011;142:148-154.
Crimi et al., Remote ischemic post-conditioning of the lower limb during primary percutaneous coronary intervention safely reduces enzymatic infarct size in anterior myocardial infarction: a randomized controlled trial. JACC Cardiovasc Interv. Oct. 2013;6(10):1055-63.
D'Ascenzo et al., Cardiac remote ischaemic preconditioning reduces periprocedural myocardial infarction for patients undergoing percutaneous coronary interventions: a meta-analysis of randomised clinical trials. EuroIntervention. Apr. 2014;9(12):1463-71. doi: 10.4244/EIJV9I12A244.
D'Ascenzo et al., Remote ischaemic preconditioning in coronary artery bypass surgery: a meta-analysis. Heart. Sep. 2012;98(17):1267-71.
Dave et al., Remote organ ischemic preconditioning protect brain from ischemic damage following asphyxial cardiac arrest. Neurosci Lett. Aug. 14, 2006;404(1-2):170-5. Epub Jun. 15, 2006.
Davies et al., Remote ischemic preconditioning improves outcome at 6 years after elective percutaneous coronary intervention: the CRISP stent trial long-term follow-up. Circ Cardiovasc Interv. Jun. 2013;6(3):246-51. Epub May 21, 2013.
Dickson et al., Rabbit heart can be "preconditioned" via transfer of coronary effluent. Am J Physiol. Dec. 1999;277(6 Pt 2):H2451-7.
Dong et al., Limb ischemic preconditioning reduces infarct size following myocardial ischemia-reperfusion in rats] Sheng Li Xue Bao. Feb. 25, 2004;56(1):41-6. Chinese, Y-Abstract.
Ghaemian et al., Remote ischemic preconditioning in percutaneous coronary revascularization: a double-blind randomized controlled clinical trial. Asian Cardiovasc Thorac Ann. Oct. 2012;20(5):548-54.
Gho et al., Myocardial protection by brief ischemia in noncardiac tissue. Circulation. Nov. 1, 1996;94(9):2193-200.
Gonzalez-Alonso et al., Haemodynamic responses to exercise, ATP infusion and thigh compression in humans: insight into the role of muscle mechanisms on cardiovascular function. J Physiol. May 1, 2008;586(9):2405-17. doi: 10.1113/jphysiol.2008.152058. Epub Mar. 13, 2008.
Gritsopoulos et al., Remote postconditioning is more potent than classic postconditioning in reducing the infarct size in anesthetized rabbits. Cardiovasc Drugs Ther. Jun. 2009;23(3):193-8. Abstract.
Gurusamy et al., Ischaemic preconditioning for liver transplantation. Cochrane Database Syst Rev. 2008:CD006315.
Hahn et al., Remote ischemic pre-conditioning: A novel therapy for acute stroke? Stroke. Aug. 2011;42:2960-2962.
Harkin et al., Ischemic preconditioning before lower limb ischemia-reperfusion protects against acute lung injury. J Vasc Surg. Jun. 2002;35(6):1264-73.
Hausenloy et al., Effect of remote ischaemic preconditioning on myocardial injury in patients undergoing coronary artery bypass graft surgery: a randomised controlled trial. Lancet. Aug. 18, 2007;370(9587):575-9.
Hausenloy et al., Preconditioning and postconditioning: underlying mechanisms and clinical application. Atherosclerosis. Jun. 2009;204(2):334-41. Epub Nov. 5, 2008.
Hausenloy et al., Remote ischaemic preconditioning: underlying mechanisms and clinical application. Cardiovasc Res. Aug. 1, 2008;79(3):377-86. doi: 10.1093/cvr/cvn114. Epub May 2, 2008.
Hausenloy et al., The therapeutic potential of ischemic conditioning: an update. Nat Rev Cardiol. Jun. 21, 2011;8(11):619-29.
Hoda et al., Remote ischemic perconditioning is effective alone and in combination with intravenous tissue-type plasminogen activator in murine model of embolic stroke. Stroke. Oct. 2012;43(10):2794-9. Epub Aug. 21, 2012.
Holcomb et al., Understanding combat casualty care statistics. J Trauma. Feb. 2006;60(2):397-401.
Hong et al., The effect of remote ischaemic preconditioning on myocardial injury in patients undergoing off-pump coronary artery bypass graft surgery. Anaesth Intensive Care. Sep. 2010;38(5):924-9.
Hoole et al., Cardiac Remote Ischemic Preconditioning in Coronary Stenting (CRISP Stent) Study: a prospective, randomized control trial. Circulation. Feb. 17, 2009;119(6):820-7. Epub Feb. 2, 2009.
Hopper et al., Role and mechanism of PKC in ischemic preconditioning of pig skeletal muscle against infarction. Am J Physiol Regul Integr Comp Physiol. Aug. 2000;279(2):R666-76.
Iliodromitis et al., Increased C reactive protein and cardiac enzyme levels after coronary stent implantation. Is there protection by remote ischaemic preconditioning? Heart. Dec. 2006;92(12):1821-6. Epub Jul. 19, 2006.
Iliodromitis et al., Intravenous atenolol and esmolol maintain the protective effect of ischemic preconditioning in vivo. Eur J Pharmacol. Sep. 19, 2004;499(1-2):163-9.
Jan et al., Limb ischemic preconditioning mitigates lung injury induced by haemorrhagic shock/resuscitation in rats. Resuscitation. Jun. 2011;82(6):760-6. Epub Mar. 12, 2011.
Jenkins et al., Ischaemic preconditioning reduces troponin T release in patients undergoing coronary artery bypass surgery. Heart. Apr. 1997;77(4):314-8.
Jennings, "A Critical Appraisal of the Revised Trauma Score," Australasian Journal of Paramedicine, vol. 2, Issue 1, (2004).
Jensen et al., Remote ischemic preconditioning protects the brain against injury after hypothermic circulatory arrest. Circulation. Feb. 22, 2011;123(7):714-721. Epub Feb. 7, 2011.
Kanoria et al., Remote ischaemic preconditioning of the hind limb reduces experimental liver warm ischaemia-reperfusion injury. Br J Surg. Jun. 2006;93(6):762-8.
Karuppasamy et al., Remote intermittent ischemia before coronary artery bypass graft surgery: a strategy to reduce injury and inflammation? Basic Res Cardiol. Jun. 2011;106(4):511-9. Epub May 5, 2011.
Kerendi et al., Remote postconditioning. Brief renal ischemia and reperfusion applied before coronary artery reperfusion reduces myocardial infarct size via endogenous activation of adenosine receptors. Basic Res Cardiol. Sep. 2005;100(5):404-12. Epub Jun. 17, 2005.
Kharbanda et al. ,"Translation of remote ischaemic preconditioning into clinical practice," Lancet, 374: pp. 1557-1565, Oct. 31, 2009.
Kharbanda et al., Ischemic preconditioning prevents endothelial injury and systemic neutrophil activation during ischemia-reperfusion in humans in vivo. Circulation. Mar. 27, 2001;103(12):1624-30.
Kharbanda et al., Remote ischaemic preconditioning protects against cardiopulmonary bypass-induced tissue injury: a preclinical study. Heart. Oct. 2006;92(10):1506-11. Epub Jul. 3, 2006.
Kharbanda et al., Transient limb ischemia induces remote ischemic preconditioning in vivo. Circulation. Dec. 3, 2002;106(23):2881-3.
Kin et al., Postconditioning attenuates myocardial ischemia-reperfusion injury by inhibiting events in the early minutes of reperfusion. Cardiovasc Res. Apr. 1, 2004;62(1):74-85.
Koch et al.,. Remote ischemic limb preconditioning after subarachnoid hemorrhage: a phase Ib study of safety and feasibility. Stroke. May 2011;42(5):1387-91. Epub Mar. 17, 2011.
Kolh Remote ischaemic pre-conditioning in cardiac surgery: benefit or not? Eur Heart J. Jan. 2014;35(3):141-3. doi: 10.1093/eurheartj/eht517. Epub Jan. 6, 2014.

(56) References Cited

OTHER PUBLICATIONS

Konstantinov et al., Remote ischemic preconditioning of the recipient reduces myocardial ischemia-reperfusion injury of the denervated donor heart via a Katp channel-dependent mechanism. Transplantation. Jun. 27, 2005;79(12):1691-5.
Konstantinov et al., The remote ischemic preconditioning stimulus modifies inflammatory gene expression in humans. Physiol Genomics. Sep. 16, 2004;19(1):143-50. Epub Aug. 10, 2004.
Konstantinov et al., The remote ischemic preconditioning stimulus modifies gene expression in mouse myocardium. J Thorac Cardiovasc Surg. Nov. 2005;130(5):1326-32.
Kottenberg et al., Protection by remote ischemic preconditioning during coronary artery bypass graft surgery with isoflurane but not propofol—a clinical trial. Acta Anaesthesiol Scand. Jan. 2012;56(1):30-8.
Kragh et al., "Practical Use of Emergency Tourniquets to Stop Bleeding in Major Limb Trauma," J Trauma 2008;64: S38-S50.
Lang et al., Myocardial preconditioning and remote renal preconditioning—identifying a protective factor using proteomic methods? Basic Res Cardiol. Mar. 2006;101(2):149-58. Epub Nov. 11, 2005.
Laskey et al., Frequency and clinical significance of ischemic preconditioning during percutaneous coronary intervention. J Am Coll Cardiol. Sep. 17, 2003;42(6):998-1003.
Lazaris et al., Protective effect of remote ischemic preconditioning in renal ischemia/reperfusion injury, in a model of thoracoabdominal aorta approach. J. Surg Res. 2009;154:267-273.
Leconte et al., Delayed hypoxic postconditioning protects against cerebral ischemia in the mouse. Stroke. Oct. 2009;40(10):3349-55. doi: 10.1161/STROKEAHA.109.557314. Epub Jul. 23, 2009.
Leesar et al., Nonelectrocardiographic evidence that both ischemic preconditioning and adenosine preconditioning exist in humans. J Am Coll Cardiol. Aug. 6, 2003;42(3):437-45.
Leesar et al., Preconditioning of human myocardium with adenosine during coronary angioplasty. Circulation. Jun. 3, 1997;95(11):2500-7.
Levy et al., Impotence and Its Medical and Psychosocial Correlates: Results of the Massachusetts Male Aging Study. J Urol. Jan. 1994;151(1):278-80.
Li et al., Late phase of myocardial ischemic preconditioning. Adv Cardiovasc Dis. Oct. 31, 2005;26(5):526-29. Chinese.
Liu et al., Remote ischemic postconditioning promotes the survival of retinal ganglion cells after optic nerve injury. J Mol Neurosci. Nov. 2013;51(3):639-46. doi: 10.1007/s12031-013-0036-2. Epub Jun. 5, 2013.
Loukogeorgakis et al., Remote ischemic preconditioning provides early and late protection against endothelial ischemia-reperfusion injury in humans: role of the autonomic nervous system. J Am Coll Cardiol. Aug. 2, 2005;46(3):450-6.
Loukogeorgakis et al., Transient limb ischemia induces remote preconditioning and remote postconditioning in humans by a K(ATP)-channel dependent mechanism. Circulation. Sep. 18, 2007;116(12):1386-95. Epub Aug. 27, 2007.
Ludman et al., Cardiac preconditioning for ischaemia: lost in translation. Dis Model Mech. Jan.-Feb. 2010;3(1-2):35-8. doi: 10.1242/dmm.003855.
McCully et al., Adenosine-enhanced ischemic preconditioning: adenosine receptor involvement during ischemia and reperfusion. Am J Physiol Heart Circ Physiol. Feb. 2001;280(2):H591-602.
Meng et al., Upper limb ischemic preconditioning prevents recurrent stroke in intracranial arterial stenosis. Neurology. Oct. 30, 2012;79(18):1853-1861. Epub Oct. 3, 2012.
Michel et al., Double blind randomized controlled crossover studies of the effects of remote preconditioning on the exercise performance of elite swimmers. Presented at The 21st Annual National Pediatric Resident and Fellow Research Competition. May 14, 2009.
Michel et al., Remote preconditioning improves maximal performance in highly trained athletes. Med Sci Sports Exerc. Jul. 2011;43(7):1280-6.

Miki et al., Captopril potentiates the myocardial infarct size-limiting effect of ischemic preconditioning through bradykinin B2 receptor activation. J Am Coll Cardiol. Nov. 15, 1996;28(6):1616-22.
Moretti et al., The EUROpean and Chinese cardiac and renal Remote Ischemic Preconditioning Study (EURO-CRIPS): study design and methods. J Cardiovasc Med (Hagerstown). May 22, 2014. [Epub ahead of print].
Mortensen et al., Limitations to systemic and locomotor limb muscle oxygen delivery and uptake during maximal exercise in humans. J Physiol. Jul. 1, 2005;566(Pt 1):273-85. Epub Apr. 28, 2005.
Mortensen et al., Restrictions in systemic and locomotor skeletal muscle perfusion, oxygen supply and VO2 during high-intensity whole-body exercise in humans. J Physiol. May 15, 2008;586(10):2621-35. doi: 10.1113/jphysiol.2007.149401. Epub Mar. 27, 2008.
Mossop, The next sports performance-enhancement fad? Blood pressure cuffs. Playbook: The Wired World of Sports. Dec. 17, 2010. Accessed from http://www.wired.com/playbook/2010/12/ischemic-preconditioning/. 4 pages.
Munk et al., High-intensity interval training may reduce in-stent restenosis following percutaneous coronary intervention with stent implantation a randomized controlled trial evaluating the relationship to endothelial function and inflammation. Am Heart J. Nov. 2009;158(5):734-741.
Munk et al., Remote ischemic conditioning in patients with myocardial infarction treated with primary angioplasty: impact on left ventricular function assessed by comprehensive echocardiography and gated single-photon emission CT. Circ Cardiovasc Imaging. Nov. 2010;3(6):656-62. Epub Sep. 8, 2010.
Murry et al., Preconditioning with ischemia: a delay of lethal cell injury in ischemic myocardium. Circulation. Nov. 1986;74(5):1124-36.
Nandagopal et al., Critical role for nitric oxide signaling in cardiac and neuronal ischemic preconditioning and tolerance. J Pharmacol Exp Ther. May 2001;297(2):474-8.
Noda et al., Evidence for the delayed effect in human ischemic preconditioning. J Amer College Cardiol. 1999;34.7:1966-74.
Olive et al., Blood flow and muscle fatigue in SCI individuals during electrical stimulation. J Appl Physiol (1985). Feb. 2003;94(2):701-8. Epub Oct. 11, 2002.
Olive et al., Increasing blood flow before exercise in spinal cord-injured individuals does not alter muscle fatigue. J Appl Physiol (1985). Feb. 2004;96(2):477-82. Epub Sep. 23, 2003.
O'riordan, Remote ischemic conditioning increases myocardial salvage during acute MI. Heartwire. Feb. 26, 2010; http://www.theheart.org/article/1050605.do, 1 page.
Oxenham et al., Angiotensin-converting enzyme inhibitor treatment after myocardial infarction. A selective approach for maximum benefit. J Am Coll Cardiol. Dec. 2000;36(7):2054-5.
Pang et al., Acute ischaemic preconditioning protects against skeletal muscle infarction in the pig. Cardiovasc Res. Jun. 1995;29(6):782-8.
Pang et al., Effector mechanism of adenosine in acute ischemic preconditioning of skeletal muscle against infarction. Am J Physiol. Sep. 1997;273(3 Pt 2):R887-95.
Pasupathy et al., Ischaemic preconditioning protects against ischaemia/reperfusion injury: emerging concepts. Eur J Vasc Endovasc Surg. Feb. 2005;29(2):106-15.
Peng et al., The protective effects of ischemic and calcitonin gene-related peptide-induced preconditioning on myocardial injury by endothelin-1 in the isolated perfused rat heart. Life Sci. 1996;59(18):1507-14.
Penttila et al., Ischemic preconditioning does not improve myocardial preservation during off-pump multivessel coronary operation. Ann Thorac Surg. Apr. 2003;75(4):1246-52; discussion 1252-3.
Peralta et al., Liver ischemic preconditioning: a new strategy for the prevention of ischemia-reperfusion injury. Transplant Proc. Aug. 2003;35(5):1800-2.
Prunier et al., The RIPOST-MI study, assessing remote ischemic perconditioning alone or in combination with local ischemic postconditioning in ST-segment elevation myocardial infarction. Basic Res Cardiol. Mar. 2014;109(2):400. doi: 10.1007/s00395-013-0400-y. Epub Jan. 10, 2014.

(56) References Cited

OTHER PUBLICATIONS

Przyklenk et al., Regional ischemic 'preconditioning' protects remote virgin myocardium from subsequent sustained coronary occlusion. Circulation. Mar. 1993;87(3):893-9.

Rahman et al., Remote ischemic preconditioning in human coronary artery bypass surgery: from promise to disappointment? Circulation. 2010;122:S53-59.

Ravio et al., Effect of remote ischemic conditioning on dendritic cell number in blood after renal transplantation—flow cytometry in a porcine model. Transpl Immunol. Mar. 2012;26(2-3):146-50. doi: 10.1016/j.trim.2011.10.006. Epub Nov. 4, 2011. Abstract only.

Redington et al., Exploring remote ischaemic preconditioning. Internal Innovation: 42-44. www.research.media.eu.

Ren et al., Limb remote ischemic postconditioning protects against focal ischemia in rats. Brain Res. Sep. 8, 2009;1288:88-94. doi: 10.1016/j.brainres.2009.07.029. Epub Jul. 23, 2009.

Ren et al., Limb remote-preconditioning protects against focal ischemia in rats and contradicts the dogma of therapeutic time windows for preconditioning. Neuroscience. Feb. 19, 2008;151(4):1099-103. Epub Dec. 15, 2007.

Rentoukas et al., Cardioprotective role of remote ischemic periconditioning in primary percutaneous coronary intervention: enhancement by opioid action. JACC Cardiovasc Interv. Jan. 2010;(3)(1):49-55.

Saxena et al., Remote ischemic conditioning: evolution of the concept, mechanisms, and clinical application. J Card Surg. Jan.-Feb. 2010;25(1):127-34. Epub Jun. 22, 2009.

Schipke et al., [Postconditioning: a brief review]. Herz. Sep. 2006;31(6):600-6. Review. German. Abstract.

Schmidt et al., Intermittent peripheral tissue ischemia during coronary ischemia reduces myocardial infarction through a KATP-dependent mechanism: first demonstration of remote ischemic perconditioning. Am J Physiol Heart Circ Physiol. Apr. 2007;292(4):H1883-90. Epub Dec. 15, 2006.

Schoemaker et al., Bradykinin mediates cardiac preconditioning at a distance. Am J Physiol Heart Circ Physiol. May 2000;278(5):H1571-6.

Sherwood, Chapter 10: Blood Vessels and Blood Pressure. Human Physiology: From Cells to Systems. 7$^{th}$ Ed. Brooks/Cole. 2008.

Shimizu et al., Effects of intermittent lower limb ischaemia on coronary blood flow and coronary resistance in pigs. Acta Physiol (Oxf). Jun. 2007;190(2):103-9. Epub Mar. 30, 2007.

Shimizu et al., Remote ischemic preconditioning decreases adhesion and selectively modifies functional responses of human neutrophils. J Surg Res. Jan. 2010;158(1):155-61.

Shimizu et al., Transient limb ischaemia remotely preconditions through a humoral mechanism acting directly on the myocardium: evidence suggesting cross-species protection. Clin Sci (Lond). Aug. 3, 2009;117(5):191-200.

Slepian et al., Pre-conditioning of smooth muscle cells via induction of the heat shock response limits proliferation following mechanical injury. Biochem Biophys Res Commun. Aug. 14, 1996;225(2):600-7.

Sloth et al., Improved long-term clinical outcomes in patients with ST-elevation myocardial infarction undergoing remote ischaemic conditioning as an adjunct to primary percutaneous coronary intervention. Eur Heart J. Jan. 2014;35(3):168-75. doi: 10.1093/eurheartj/eht369. Epub Sep. 12, 2013.

Sloth et al., Remote ischemic perconditioning improves long-term clinical outcome in patients undergoing primary percutaneous coronary intervention for ST-Elevation myocardial infarction. J Amer Coll Cardiol. Oct. 23, 2012;60(17):B20. Abstract TCT-63.

Soendergaard et al. Improved GGF and renal plasma perfusion following remote ischaemic conditioning in a porcine kidney transplantation model. Transpl Int. Sep. 2012;25(9):1002-12. doi: 10.1111/j.1432-2277.2012.01522.x. Epub Jul. 6, 2012.

Spargias et al., Beta blocker treatment and other prognostic variables in patients with clinical evidence of heart failure after acute myocardial infarction: evidence from the Aire study. Heart. Jan. 1999;81(1):25-32.

Steensrud et al., Pretreatment with the nitric oxide donor SNAP or nerve transection blocks humoral preconditioning by remote limb ischemia or intra-arterial adenosine. Am J Physiol Heart Circ Physiol. Nov. 2010;299(5):H1598-603. doi:10.1152/ajpheart.00396. 2010. Epub Aug. 27, 2010.

Sun et al., Postconditioning attenuates cardiomyocyte apoptosis via inhibition of JNK and p38 mitogen-activated protein kinase signaling pathways. Apoptosis. Sep. 2006;11(9):1583-93.

Takano et al., Late preconditioning enhances recovery of myocardial function after infarction in conscious rabbits. Am J Physiol Heart Circ Physiol. Nov. 2000;279(5):H2372-81.

Takarada et al., Applications of vascular occlusion diminish disuse atrophy of knee extensor muscles. Med Sci Sports Exerc. Dec. 2000;32(12):2035-9.

Tan et al., Late phase of remote ischemic preconditioning. Chongqing Medicine. Aug. 31, 2007;36(16):1608 and 1610. Chinese.

Tanaka et al., Expression of heat shock protein after ischemic preconditioning in rabbit hearts. Jpn Circ J. Jul. 1998;62(7):512-6.

Tejwani NC et al., "Tourniquet Cuff Pressure: The Gulf Between Science and Practice," J. Trauma, 61 (6), pp. 1415-1418, Dec. 2006. Abstract only.

Thielmann et al., Remote ischemic preconditioning reduces myocardial injury after coronary artery bypass surgery with crystalloid cardioplegic arrest. Basic Res Cardiol. Sep. 2010;105(5):657-64. Epub May 21, 2010.

Thielmann et al., Remote ischemic preconditioning: the surgeon's perspective. J Cardiovasc Med (Hagerstown). Oct. 1, 2012;13:1-6 [Epub ahead of print].

Thijssen et al., Assessment of flow-mediated dilation in humans: a methodological and physiological guideline. Am J Physiol Heart Circ Physiol. Jan. 2011;300(1):H2-12. doi: 10.1152/ajpheart.00471. 2010. Epub Oct. 15, 2010.

Thuny et al., Post-conditioning reduces infarct size and edema in patients with ST-segment elevation myocardial infarction. J Am Coll Cardiol. Jun. 12, 2012;59(24):2175-81.

Toledo-Pereyra et al., Molecular signaling pathways in ischemia/reperfusion. Exp Clin Transplant. Jun. 2004;2(1):174-7.

Tomai et al., Ischemic preconditioning in humans: models, mediators, and clinical relevance. Circulation. Aug. 3, 1999;100(5):559-63.

Venugopal et al., Remote ischaemic preconditioning reduces myocardial injury in patients undergoing cardiac surgery with cold-blood cardioplegia: a randomised controlled trial. Heart. Oct. 2009;95(19):1567-71. Epub Jun. 8, 2009.

Venugopal et al., Effect of remote ischemic preconditioning on acute kidney injury in nondiabetic patients undergoing coronary artery bypass graft surgery: a secondary analysis of 2 small randomized trials. Am J Kidney Dis. Dec. 2010; 5(6): 1043-9.

Vinten-Johansen et al., Postconditioning—A new link in nature's armor against myocardial ischemia-reperfusion injury. Basic Res Cardiol. Jul. 2005;100(4):295-310. Epub Mar. 30, 2005.

Wagner et al., Myocardial injury is decreased by late remote ischaemic preconditioning and aggravated by tramadol in patients undergoing cardiac surgery: a randomised controlled trial. Interact Cardiovasc Thorac Surg. Dec. 2011;11(6):758-62. doi: 10.1510/icvts.2010.243600. Epub Sep. 16, 2010.

Walsh et al., Remote ischemic preconditioning for renal and cardiac protection during endovascular aneurysm repair: a randomized controlled trial. J Endovasc Ther. Dec. 2009;16(6):680-9.

Wang et al., Remote ischemic preconditioning by hindlimb occlusion prevents liver ischemic/reperfusion injury: the role of High Mobility Group—Box 1. Ann Surg. Feb. 2010;251(2):292-9. doi: 10.1097/SLA.0b013e3181bfda8c.

Wang et al., Remote Ischemic Preconditioning Protects against Liver Ischemia-Reperfusion Injury via Heme Oxygenase-1-Induced Autophagy. PLoS One. Jun. 10, 2014;9(6):e98834. doi 10.1371/journal.pone.0098834. eCollection 2014. 12 pages.

Warzecha et al., Ischaemic preconditioning of the hundlimb or kidney does not attenuate the severity of acute ischemia/reperfusion-induced pancreaitis in rats. J Physiol Pharmacol. Jun. 2008;59(2):337-52.

Wei et al., Repeated remote ischemic postconditioning protects against adverse left ventricular remodeling and improves survival in

(56) References Cited

OTHER PUBLICATIONS a rat model of myocardial infarction. Circ Res. May 13, 2011;108(10):1220-5. Epub Apr. 7, 2011. Supplemental Information Included.

Whittaker et al., Remote-conditioning ischemia provides a potential approach to mitigate contrast medium-induced reduction in kidney function: a retrospective observational cohort study. Cardiology. 2011;119(3):145-50. doi: 10.1159/000330930. Epub Sep. 23, 2011.

Wolfrum et al., Calcitonin gene related peptide mediates cardioprotection by remote preconditioning. Regul Pept. Apr. 15, 2005;127(1-3):217-24.

Xie et al., Remote ischaemic preconditioning reduces myocardial injury in patients undergoing heart valve surgery: randomised controlled trial. Heart. Mar. 2012;98(5):384-8. Epub Nov. 22, 2011.

Xin et al., Combined local ischemic postconditioning and remote perconditioning recapitulate cardioprotective effects of local ischemic preconditioning. Am J Physiol Heart Circ Physiol. Jun. 2010;298(6):H1819-31. Epub Mar. 5, 2010. Erratum in: Am JPhysiolHeart Circ Physiol. Sep. 2010;299(3):H957.

Yellon et al., Preconditioning the myocardium: from cellular physiology to clinical cardiology. Physiol Rev. Oct. 2003;83(4):1113-51.

Zhang et al., [Correlation of limb and myocardial ischemia postconditioning with acute myocardial reperfusion injury]. Zhonghua Yi Xue Za Zhi. Mar. 28, 2006;86(12):841-5. Chinese. (Abstract Only).

Zhao et al., Inhibition of myocardial injury by ischemic postconditioning during reperfusion: comparison with ischemic preconditioning. Am J Physiol Heart Circ Physiol. Aug. 2003;285(2):H579-88.

Zhao, Ischemic postconditioning as a novel avenue to protect against brain injury after stroke. J Cereb Blood Flow Metab. May 2009;29(5):873-85. doi: 10.1038/jcbfm.2009.13. Epub Feb. 25, 2009.

Zhou et al., Limb ischemic preconditioning reduces heart and lung injury after an open heart operation in infants. Pediatr Cardiol. Jan. 2010;31(1):22-9. Epub Sep. 29, 2009.

Zimmerman et al., Ischemic preconditioning at a remote site prevents acute kidney injury in patients following cardiac surgery. Kidney Int. 2011;80:861-867.

Zografos et al., Remote ischemic preconditioning reduces periprocedural myocardial injury in elective percutaneous coronary intervention: a meta-analysis. Int J Cardiol. May 15, 2014;173(3):530-2. doi: 10.1016/j.ijcard.2014.03.026. Epub Mar. 15, 2014.

International Search Report and Written Opinion for Application No. PCT/IB2014/000922 dated Sep. 26, 2014.

International Preliminary Report on Patentability for Application No. PCT/IB2014/000922 dated Sep. 24, 2015.

[No Author Listed] Highlights of Prescribing Information. CIALIS (tadalafil) tablets, for oral use. Initial U.S. Approval: 2003. May 2017. 29 pages.

* cited by examiner

TREATMENT OF ERECTILE DYSFUNCTION USING REMOTE ISCHEMIC CONDITIONING

RELATED APPLICATIONS

This application is a national stage filing under 35 U.S.C. § 371 of International Application No. PCT/IB2014/000922, filed Mar. 12, 2014, which claims the benefit under 35 U.S.C. § 119(e) of U.S. Provisional Application No. 61/801, 006, filed Mar. 15, 2013, and entitled "TREATMENT OF ERECTILE DYSFUNCTION USING REMOTE ISCHEMIC CONDITIONING," the entire contents of both of which are incorporated herein by reference.

FIELD OF THE INVENTION

The invention provides methods and compositions for treatment of erectile dysfunction using remote ischemic conditioning.

BACKGROUND OF INVENTION

Remote ischemic conditioning (RIC) is a process whereby brief repetitive periods of ischemia (e.g. in a limb) followed by reperfusion. RIC has been are used to induce resistance to subsequent ischemic injury in an organ remote from the limb (e.g. the heart).

RIC has been shown to be useful in the treatment of ischemic and/or reperfusion injury. Thus, RIC has been contemplated primarily for myocardial infarction and ensuing heart failure, restenosis, and traumatic injury including trauma associated with hypovolemic shock. RIC has also been contemplated as an adjunct to surgery such as cardiovascular surgery. RIC has also been reported to provide performance enhancement to healthy subjects including elite swimmers as well as subjects having conditions that impair exercise (e.g., cardiovascular disease). In some instances, the subjects to be treated according to the invention may be subjects that would not have been previously contemplated for RIC therapy.

SUMMARY OF INVENTION

The invention contemplates use of remote ischemic conditioning (RIC) to treat erectile dysfunction.

Thus, in one aspect, the invention provides a method comprising performing remote ischemic conditioning (RIC) or a RIC-like intervention on a subject that has experienced, is experiencing, or is at risk of experiencing erectile dysfunction.

In some embodiments, the subject has experienced at least one ED event. In some embodiments, the at least one ED event occurred within a month, within a week, or within a day.

In some embodiments, RIC is performed on the subject. In some embodiments, the RIC is chronic RIC. In some embodiments, the RIC is acute RIC.

In some embodiments, RIC is performed on a daily basis. In some embodiments, RIC is performed more than once a day. In some embodiments, RIC is performed within 24 hours, within 12 hours, within 6 hours, within 4 hours, within 2 hours, within 1 hour, or within 30 minutes prior to intercourse or other activity requiring an erect penis.

In some embodiments, RIC comprises 1, 2, 3, 4, 5 or more cycles, each cycle comprising a blood occlusion period and a reperfusion period. In some embodiments, RIC comprises one or more cycles, each cycle comprising a 5 minute blood occlusion period and a 5 minute reperfusion period.

In some embodiments, RIC is performed repeatedly at the same site. In some embodiments, RIC is performed repeatedly on an upper limb. In some embodiments, RIC is performed repeatedly on a lower limb.

In some embodiments, a RIC-like intervention is performed on the subject. In some embodiments, the RIC-like intervention is non-invasive electrical nerve stimulation.

In some embodiments, the subject is receiving a second therapy to treat erectile dysfunction. In some embodiments, the second therapy is administered at less than a maximum tolerable dose. In some embodiments, the second therapy is administered at greater than the maximum tolerable dose.

Non-limiting embodiments of the present invention will be described by way of example with reference to the accompanying figures, which are schematic and are not intended to be drawn to scale. For purposes of clarity, not every component is labeled in every figure, nor is every component of each embodiment of the invention shown where illustration is not necessary to allow those of ordinary skill in the art to understand the invention.

DETAILED DESCRIPTION OF INVENTION

The invention provides for use of remote ischemic conditioning (RIC) including acute or chronic RIC to treat erectile dysfunction. ED may also be known as sexual dysfunction to the extent such latter dysfunction relates to an inability to obtain and/or maintain an erection.

The invention relates to treating subjects that have experienced ED and those that are at risk of experiencing ED. Subjects at risk of experiencing ED may be at risk due to family history, or due to exposure to one or more agents, or due to lifestyle and environment.

Subjects at risk of experiencing ED may have another condition or disorder. For example, ED has been associated with endocrine disorders, e.g., testicular failure and hyperprolactinemia; side effects of drugs, e.g., antiandrogens, antihypertensives, anticholinergics, antidepressants, antipsychotics, central nervous system depressants and drugs of habituation or addiction; penile diseases, e.g., Peyronie's disease, previous priapism, and penile trauma; neurological diseases, e.g., anterior temporal lobe lesions, diseases of the spinal cord, loss of sensory input, diseases of nervi erigentes, and diabetic autonomic neuropathy; and vascular diseases, e.g., essential hypertension, aortic occlusion, atherosclerotic occlusion or stenosis of the pudendal artery, venous leak, and diseases of the sinusoid spaces. The invention intends to treat subjects that are at risk of experiencing ED (but who have not yet experienced ED) and who may have one of these conditions. The invention also intends to treat subjects that have experienced ED and who may one of these conditions.

In some instances, subjects to be treated in accordance with the invention may or may not have essential hypertension, coronary artery disease, and/or diabetes.

In some instances, the subjects may not be experiencing, may not have experienced, and/or may not be at risk of experiencing a myocardial infarction, or a restenotic event, or a traumatic injury.

In some embodiments, RIC is not performed within a week, 6 days, 5 days, 4 days, 3 days, 2 days, 1 day, 12 hours, 6 hours, 4 hours, 2 hours, or 1 hour prior to athletic activity (other than intercourse).

A subject includes but is not limited to humans and other non-human animals including, for example, companion animals such as dogs, cats, domesticated pigs, ferrets, hamsters, and the like; primates such as monkeys, and the like; agricultural animals such as cattle, pigs, horses, sheep, goats; prize-winning animals such as thoroughbreds, and the like. In important embodiments, the subject is a human subject.

Generally, to treat, as used herein, encompasses to prevent, to delay, or to ameliorate, as appropriate, development or continuance or aggravation of ED in a subject or to relieve, reduce or alleviate at least one symptom of associated with ED or to reduce the frequency of an ED event or to reduce the likelihood of reoccurrence of an ED event (or ED altogether). An ED event, as used herein, is an inability to achieve an erection at a given time (for example in preparation for intercourse). Treatment can be diminishment of one or several symptoms of ED or complete eradication of ED. Within the meaning of the present invention, the term treat also denotes to arrest, delay the onset (i.e., the period prior to clinical manifestation of ED) and/or reduce the risk of developing or worsening ED.

The invention includes treating subjects using RIC and/or a RIC-like intervention alone or in combination with one or more other therapies used to treat ED RIC may be performed chronically (chronic RIC) or it may performed acutely (acute RIC).

Remote Ischemic Conditioning (RIC)

Remote ischemic conditioning (RIC), as used herein, refers to a non-invasive process of deliberately inducing an ischemic event or period (typically by occluding arterial blood flow) followed by a reperfusion event or period (typically where blood is allowed to reperfuse) that is typically performed on an upper or lower limb or on a region of the body that is remote from an organ or tissue that is intended to benefit from the process itself. RIC may be contrasted with local ischemic conditioning which involves blood flow occlusion and reperfusion in a tissue or organ or region of the body to be protected from an existing or a future anticipated ischemia/reperfusion injury and it typically an invasive procedure. An example is local IC of the heart prior to cardiac surgery.

RIC may be performed as a single cycle (i.e., one ischemic event followed by one reperfusion event) or as multiple cycles. Multiple cycles include but are not limited to two, three, four, five or more cycles. The one or multiple cycles, when performed consecutively without significant delay, are referred to a RIC regimen or treatment.

The blood flow restriction (or occlusion) typically takes the form of an applied pressure to the limb that is sufficient to occlude blood through the limb. In some instances, the occlusive blood pressure is above systolic pressure (i.e., supra-systolic pressure). It may be about 5, about 10, about 15, about 20, or more mmHg above (or greater than) systolic pressure. In some instances, the occlusive blood pressure may be at or below systolic pressure. Since systolic pressure will differ between subjects, the absolute pressure needed to induce ischemia will vary between subjects. In other embodiments the pressure may be preset at, for example, 200 mmHg. The blood flow restriction may be accomplished using any method or device provided it is capable of inducing transient ischemia and reperfusion, whether manually or automatically. Such devices include without limitation a manually inflatable cuff, or an automated device as described below. The devices comprise cuffs of standard width or cuffs of greater than standard width.

The induced ischemic event or period is transient. That is, it may have a duration of about 1, about 2, about 3, about 4, about 5, or more minutes. Similarly, the reperfusion event or period may have a duration of about 1, about 2, about 3, about 4, about 5, or more minutes.

One or both upper limbs or one or both lower limbs may be used although in some instances one or both upper limbs are preferred. In some instances, RIC is performed on two different sites on the body, in an overlapping or simultaneous manner.

Devices for performing RIC are also known in the art, and include those described in U.S. Pat. No. 7,717,855 and US patent application publication 2012/0265240 A1, both of which are incorporated herein by reference in their entirety. Briefly, this system comprises a cuff configured to retract about a limb of a subject, an actuator connected to the cuff that when actuated causes the cuff to contract about the limb of the subject to reduce blood flow therethrough, and a controller that controls the actuator according to a treatment protocol. The treatment protocol typically includes a plurality of treatment cycles, each of which may comprise a cuff actuation period during which the actuator contracts the cuff about the limb of the subject to a pressure that occludes blood flow through the limb, an ischemic duration period during which the actuator maintains the cuff contracted about the limb at a set pressure point to occlude blood flow through the limb, a cuff release period during which the actuator releases the cuff to allow blood flow through the limb, and a reperfusion period during which the cuff is maintained about the limb in a relaxed state to allow blood flow through the limb.

Acute RIC

Acute RIC, as used herein, refers to the use of RIC in a relatively short time frame around intercourse (or other event requiring an erect penis). When performed acutely, RIC may be performed one or more times within 1 week, within 5 days, within 4 days, within 3 days, within 2 days, within 1 day, within 12 hours, within 6 hours, within 4 hours, within 2 hours, within 1 hour, within 30 minutes, within 20 minutes, or within 10 minutes prior to intercourse (or other event requiring an erect penis).

Chronic RIC

In some instances, chronic RIC may be used to treat ED. As used herein, chronic RIC means performing a RIC regimen (which itself may comprise 1, 2, 3, 4, 5, or more cycles of ischemia and reperfusion) more than once over the course of more than one day. Chronic RIC encompasses daily performance of a RIC regimen, weekly performance of a RIC regimen, bi-weekly performance of a RIC regimen, monthly performance of a RIC regimen, including performance that is more or less frequent. Chronic RIC also encompasses performing a RIC regimen every other day, every third day, every fourth day, every fifth day, or every sixth day. The RIC regimens may be identical to each other or they may differ. Chronic RIC encompasses scheduled RIC regimens (e.g., non-random RIC regimens) or random RIC regimens (e.g., performing RIC when a subject feels the need rather than on a set schedule). Chronic RIC also contemplates that more than one RIC regimen may be performed on a single day.

RIC-Like Interventions

RIC-like interventions include but are not limited to non-invasive electrical nerve stimulation such as transcutaneous electrical nerve stimulation, direct nerve stimulation such as femoral nerve stimulation, electro-acupuncture, nociceptive c-fiber stimulation for example via topical capsaicin, and intra-arterial adenosine.

As used herein, non-invasive electrical nerve stimulation may be a single cycle of nerve stimulation followed by a rest period during which no current is applied to the subject, or it may be repeated cycles of nerve stimulation followed by a rest period. The repeated cycles may comprise 2, 3, 4, 5 or more cycles of nerve stimulation followed by a rest period. For clarity, two cycles of non-invasive electrical nerve stimulation would consist of a nerve stimulation period, a rest period, a nerve stimulation period, and a rest period. The invention contemplates that, in some embodiments, a single nerve stimulation period may be sufficient to achieve the desired therapeutic, prophylactic or performance endpoints.

The nerve stimulation period and the rest period may each range from 30 seconds to several minutes or hours. Either or both periods may be up to or about 30 seconds, or 1, 2, 3, 4, 5, 6, 7, 8, 9, 10, 15, 20, 25, 30, 35, 40, 45, 50, 55 or 60 minutes in duration, or longer. The two periods may or may not be of the same duration. An exemplary non-invasive electric nerve stimulation comprises 4 or 5 cycles of 5 minutes of nerve stimulation followed by 5 minutes of rest. Another exemplary non-invasive electrical nerve stimulation comprises 4 or 5 cycles of 4 minutes of nerve stimulation followed by 4 minutes of rest.

The non-invasive electrical nerve stimulation device may be operated under any number of pulse amplitude (or intensity), pulse width, and pulse frequency settings. As an example, the pulse amplitude may range from 1 to 200 mA, including typically from 1 to 100 mA, from 1 to 90 mA, from 1-80 mA, from 1-70 mA, from 1-60 mA, from 1-50 mA, from 1-40 mA, from 1-30 mA, from 1-20 mA, from 1-15 mA, from 1-10 mA, from 1-9 mA, from 1-8 mA, from 1-7 mA, from 1-6 mA, from 1-5 mA, from 1-4 mA, from 1-3 mA, or from 1-2 mA. The pulse frequency may range from 1 to 300 Hz, including typically from 1 to 150 Hz, from 1-140 Hz, from 1-130 Hz, from 1-120 Hz, from 1-110 Hz, from 1-100 Hz, from 1-90 Hz, from 1-80 Hz, from 1-70 Hz, from 1-60 Hz, from 1-50 Hz, from 1-40 Hz, from 1-30 Hz, from 1-20 Hz, from 1-10 Hz, from 1-9 Hz, from 1-8 Hz, from 1-7 Hz, from 1-6 Hz, from 1-5 Hz, from 1-4 Hz, from 1-3 Hz, or from 1-2 Hz. The pulse width may range up to 1 to 1600 microseconds, including typically from 1 to 800 microseconds, from 1-700 milliseconds, from 1-600 milliseconds, from 1-500 milliseconds, from 1-400 milliseconds, from 1-300 milliseconds, from 1-200 milliseconds, from 1-100 milliseconds, and from 1-50 milliseconds. The device may also operate at a voltage typically up to 80 V, including typically up to 40 V, up to 30 V, up to 20 V, up to 10 V, and up to 5 V. Exemplary settings include a pulse amplitude of 2-3 mA, a pulse frequency of 3.1 Hz, and a pulse width of 500 microseconds.

Non-invasive electrical nerve stimulation may be performed at any site on the body that is amenable to the non-invasive procedure. It may be performed on any outer surface of the body, including but not limited to arms, legs, feet, hands, torso, chest, back, and the like. It may be performed at a remote site (i.e., a site that is distal to the area of the body experiencing or likely to experience the ischemic and/or reperfusion injury). In other words, the placement of the electrodes may be distal to the region of the body being treated. As an example, the electrodes may be placed on the legs in order to reduce injury in the heart. Typically at least two electrodes are placed within proximity of each other in order to allow current to flow therebetween. Additional paired electrodes may be used at the same or different surface region of the body at the same or different time.

Repeated non-invasive electrical nerve stimulations may be performed at a single, identical site or at multiple, different sites on the body. As an example, a first stimulation may be performed on the right upper arm, followed by a second stimulation performed on the left upper arm. In some embodiments, the non-invasive electrical nerve stimulation is not performed on the chest. Repeated non-invasive electrical nerve stimulations may alternate between two sites or they may cycle through more than two sites. In some instances, non-invasive electrical nerve stimulation may be performed on a subject at two different sites at overlapping times including simultaneously. The use of more than one location may be determined a priori or it may be random. When multiple locations are used simultaneously, two or more devices are typically used.

RIC and RIC-Like Intervention as Adjunct Therapy or in Combination Therapy

The invention includes the use of RIC and/or RIC-like interventions as a stand alone or in combination with another therapy. When used together with another therapy, in some instances, RIC and/or RIC-like interventions may reduce the adverse effects of the other therapy. In other instances, RIC and/or RIC-like therapy may synergize with the other therapy, resulting in a greater than additive effect when both therapies are used together (as compared to when they are used separately and thus independently). In some instances, the invention contemplates using RIC and/or RIC-like interventions with a dose of another therapy that is less than the dose that would otherwise be required if the other therapy was administered alone. Dose reductions may be 1%, 2%, 3%, 3%, 4%, 5%, 6%, 7%, 8%, 9%. 10%, 20% or more. Dose reductions can also take the form of less frequent administration of the other therapy.

Therapies used to treat ED include ED agents such as but not limited to Angiotensin II antagonists, ACE inhibitors, Specific therapies to treat ED include Sildenafil (Viagra), Tadalafil (Cialis), Vardenafil (Levitra), atipamezole, alprostadil, and Sibutramine.

Other therapies for ED include mechanical interventions such as implanted balloons that can be manually or automatically inflated.

OTHER EMBODIMENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Each reference recited herein is incorporated by reference herein in its entirety.

What is claimed is:

1. A method for treating erectile dysfunction comprising performing remote ischemic conditioning (RIC) on a subject that has experienced or is experiencing erectile dysfunction, to treat erectile dysfunction,
wherein RIC comprises two cycles, each cycle comprises a one minute of blood flow occlusion period followed by a reperfusion period, and wherein a second or subsequent cycle begins upon conclusion of the reperfusion period of a previous cycle.

2. The method of claim 1, wherein the RIC is chronic RIC.

3. The method of claim 1, wherein the RIC is acute RIC.

4. The method of claim 2, wherein RIC is performed on a daily basis.

5. The method of claim 2, wherein RIC is performed more than once a day.

6. The method of claim 3, wherein RIC is performed within 24 hours, within 12 hours, within 6 hours, within 4 hours, within 2 hours, within 1 hour, or within 30 minutes prior to intercourse or other activity requiring an erect penis.

7. The method of claim 1, wherein RIC comprises 3, 4, or 5 cycles.

8. The method of claim 1, wherein each cycle comprises a 5 minute blood occlusion period and a 5 minute reperfusion period.

9. The method of claim 1, wherein RIC is performed repeatedly at the same site.

10. The method of claim 9, wherein RIC is performed repeatedly on an upper limb.

11. The method of claim 9, wherein RIC is performed repeatedly on a lower limb.

12. The method of claim 1, wherein the subject is receiving a second therapy to treat erectile dysfunction.

13. The method of claim 12, wherein the second therapy is administered at less than a maximum tolerable dose.

14. The method of claim 12, wherein the second therapy is administered at greater than a maximum tolerable dose.

* * * * *